United States Patent [19]

Guirguis

[11] Patent Number: 5,358,690
[45] Date of Patent: * Oct. 25, 1994

[54] ENVIRONMENTAL SAMPLE COLLECTION AND MEMBRANE TESTING DEVICE

[75] Inventor: Raouf A. Guirguis, Rockville, Md.

[73] Assignee: LaMina, Ltd., Fairfax, Va.

[ * ] Notice: The portion of the term of this patent subsequent to Dec. 31, 2008 has been disclaimed.

[21] Appl. No.: 814,447

[22] Filed: Dec. 30, 1991

Related U.S. Application Data

[63] Continuation-in-part of Ser. No. 506,070, Apr. 9, 1990, Pat. No. 5,077,012, which is a continuation-in-part of Ser. No. 308,763, Jan. 10, 1989, Pat. No. 4,961,432, and a continuation-in-part of Ser. No. 440,117, Nov. 22, 1989, Pat. No. 5,022,411.

[51] Int. Cl.$^5$ ............................................. G01N 21/00
[52] U.S. Cl. ................................. 422/58; 422/56; 435/288; 435/296; 435/975; 436/63; 436/165
[58] Field of Search ................. 422/58, 102, 56; 604/317; 128/771; 435/296, 975, 6, 7.31, 7.36, 7.35, 7.32, 291, 288; 436/518, 807, 810, 63, 165

[56] References Cited

U.S. PATENT DOCUMENTS

| | | | |
|---|---|---|---|
| 3,312,221 | 4/1967 | Overment | 128/275 |
| 3,817,837 | 6/1974 | Rubenstein et al. | 436/546 |
| 4,353,868 | 10/1982 | Joslin et al. | 422/102 |
| 4,374,925 | 2/1983 | Litman et al. | 435/5 |
| 4,473,530 | 9/1984 | Villa-Real | 422/58 |
| 4,492,258 | 1/1985 | Lichtenstein et al. | 141/1 |
| 4,573,983 | 3/1986 | Annis | 604/322 |
| 4,632,901 | 12/1986 | Valkirs et al. | 435/5 |
| 4,661,100 | 4/1987 | Rechsteiner | 604/327 |
| 4,685,472 | 8/1987 | Muto | 128/760 |
| 4,729,875 | 3/1988 | Chandler | 422/58 |
| 4,797,260 | 1/1989 | Parker | 422/101 |
| 4,823,461 | 4/1989 | Takahashi et al. | 29/612 |
| 4,953,561 | 9/1990 | Guirguis | 128/771 |
| 5,016,644 | 5/1991 | Guirguis | 128/771 |
| 5,022,411 | 6/1991 | Guirguis | 128/771 |
| 5,024,237 | 6/1991 | Guirguis | 128/760 |
| 5,026,653 | 6/1991 | Lee et al. | 422/58 |
| 5,038,793 | 8/1991 | Guirguis | 128/760 |
| 5,077,012 | 12/1991 | Guirguis | 422/58 |

FOREIGN PATENT DOCUMENTS

| | | | |
|---|---|---|---|
| 246760 | 11/1987 | European Pat. Off. | G01N 33/53 |
| WO88/00345 | 1/1988 | PCT Int'l Appl. | G01N 33/543 |
| WO90/00251 | 1/1990 | PCT Int'l Appl. | G01N 21/78 |

*Primary Examiner*—James C. Housel
*Assistant Examiner*—Laura E. Collins
*Attorney, Agent, or Firm*—Beveridge, DeGrandi, Weilacher & Young

[57] ABSTRACT

An apparatus for collecting fluids and holding samples taken from the fluid for qualitative and quantitative testing. The apparatus comprises a tubular container open at both ends with a quantitative test storage unit removably secured to one of said tubular container ends. The quantitative test storage unit has an open end, a cytology membrane mounted in the storage unit and a retaining rib. A shuttle assembly is slidably mounted in the tubular container comprising a cylindrical hollow piston defining a chamber, a thumb cover covering one end of the piston and a fluid flow aperture formed in the piston and a qualitative sample container assembly removably secured to the piston. The qualitative sample container assembly comprises a clip on membrane assembly including a membrane containing immobilized antibodies and a filter housing mounted to the clip on membrane assembly. The filter housing is adapted to be seated in the quantitative test storage unit after being slidably transported along the tubular container by the piston.

30 Claims, 4 Drawing Sheets

ENVIRONMENTAL SAMPLE COLLECTION AND MEMBRANE TESTING DEVICE

RELATED CASES

This is a continuation-in-part application of U.S. patent application Ser. No. 07/506,070 filed Apr. 9, 1990, now U.S. Pat. No. 5,077,012, issued Dec. 13, 1991, which is a continuation-in-part application of U.S. patent application Ser. No. 07/308,763 filed Jan. 10, 1989, now U.S. Pat. No. 4,961,432, issued Oct. 9, 1990, and U.S. patent application Ser. No. 07/440,117 filed Nov. 22, 1989, now U.S Pat. No. 5,022,411, issued Jun. 11, 1991.

BACKGROUND OF THE INVENTION

1. Field of the Invention

The present invention is directed to an apparatus for determining the presence of microorganisms, chemicals, and other analytes in physiological, biological and environmental specimens. Thus the present invention performs diagnostic tests for pathogenic organisms, detection and identification of toxin and drug contamination in food for human and animal consumption and monitoring for pesticide residues in water, soil and food.

2. Description of the Prior Art

As used in this specification the word "analyte" is a term from analytical chemistry meaning the compound for which an assay is developed (e.g., a mycotoxin, its metabolite, and toxin-DNA adducts are all different analytes that might be detected by different assays).

Almost all physiological, biological and environmental fluids are composed of a liquid phase (solvent) and a non-liquid phase. The non-liquid phase consists of two main constituents: i) insoluble substance (i.e. solids, and sediments ) such as microorganisms, cellular debris, crystals, and particles; and ii) soluble substances (i.e. solutes) such as organic and inorganic substances.

For detection of any abnormalities and/or contaminants of such fluids, the fluid constituents must be separated or extracted from the liquid phase to allow for specialized testing being performed. This has been accomplished by a series of processes involving a number of different containers and expensive laboratory equipment. Examples of these processes include: separation of insoluble matter using filtration and/or centrifugation; and solid-phase extraction of soluble substances. Once the fluid constituent is isolated from the liquid phase a series of qualitative and/or quantitative tests can be performed to determine the presence or absence of the analyte and measure its concentration in solution. Examples of these tests include Immunoassays (IA), Solid-Phase Extraction (SPE) using Gas and Liquid Chromatography (GC,LC), Mass Spectrometry (MS), cell culturing on special media, in situ Hybridization using DNA and/or RNA probes, DNA and/or RNA target and signal amplification using Polymerase Chain Reaction (PCR). Mass testing using such a series of processes is expensive, time consuming, and often unsatisfactory.

Specialized Testing using Insoluble Substances

Detection and identification microorganisms

The traditional methods of detecting and identifying microorganisms in physiological and biological fluids require cell culturing on laboratory media (sometimes followed by susceptibility testing to determine resistance to a particular antibiotic), identification of the organism by detection of serum antibodies against the organism. These methods may require 24 hours to ten days to perform and therefore do not necessarily contribute toward patient management and diagnosis. In some cases the microorganism cannot be isolated or cultured. The use of cytology cups and membranes to isolate cells or microorganisms from wide variety of fluids is known in the art. The Nuclepore Schisto-Kit TM is designed for rapid and accurate quantification of Schistosome eggs in urine by the membrane filtration technique. A simple syringe filtration permits collection of virtually all eggs onto the smooth flat surface of a transparent Nuclepore polycarbonate membrane filter. Quantitative egg counts without staining are easily made with a low power magnifier. Other cytology cups are marketed under the trademark SWIN-LOCK and Swinnex Disc Filter Holder. Nuclepore polycarbonate membranes are used for diagnostic cytology. The surface allows collection of atypical cells from all types of body fluids. More recently the use of Polymerase Chain Reaction (PCR) as a DNA and/or RNA target and signal amplification system and the use of nucleotide probes coupled with in situ hybridization techniques have opened the door to a more sensitive and specific tests for identification of the organism. However, these tests as much as other laboratory tests demand minimal manipulations of the sample being tested to minimize potential sample contaminations and consequently very high rate of false test results.

Specialized Testing using Soluble Substances

A. Solid Phase Extraction

Solid phase extraction has rapidly gained acceptance as an efficient, reproducible sample preparation technique. In solid phase extraction, chromatographic sorbents (usually bonded phases) are used to selectively separate analytes and/or interfering impurities from a sample matrix. Solid phase extraction offers a range of selectively that cannot be achieved with traditional liquid/liquid extraction techniques. Chromatographic columns have been developed for selective isolation or concentration of interesting components from a complex mixture or a large sample volume. For this solid phase extraction (also known as SPE) one takes advantage of different types of interactions (non-polar, polar, or ion exchange) between the sample components, a solid sorbent and a suitable eluent. By selection of the appropriate sorbent interaction (Polar, Hydrophobic, and Ionic) the analyst can utilize the solid phase to separate a wide range of analytes and/or interfering impurities from the sample matrix. Contrary to conventional liquid-liquid extraction solid phase extraction saves solvent and time. Due to combination of different interactions the method features a high degree of versatility. Additionally problems such as long times for phase separation or formation of stable emulsions do not occur. In liquid-liquid extraction this can only be achieved by multiple extractions. Besides selective fractionation another application of solid phase extraction is enrichment of substances from dilute solutions for trace determinations, since interesting components can be absorbed from a large sample volume and eluted with a small amount of solvent.

B. Affinity Chromatography

Affinity chromatography is a powerful technique for separating molecules based on specific binding to sites on proteins or other biopolymers. Affinity chromatography can be used for either analytical or preparative separations. The material of interest can be a macromolecule such as a protein, in which case a specific small ligand may be immobilized on the stationary phase matrix to cause retention or the ligand immobilized on the column can be a protein which interacts specifically with another substance, usually a macromolecule, to cause retention. Nucleic acids can also be immobilized, creating the possibility of retention by specific base sequence recognition. Affinity chromatography is ordinarily a simple two-step process. A solution containing the substance of interest is forced through the affinity column under conditions favoring specific interaction. This causes the material of interest to become attached to the column while other substances pass directly through. The column is washed with a solution that weakens the specific binding interaction, and the material of interest is immediately eluted from the column in greatly purified form.

C. Immunoassays

Immunochemical detection is based on the ability of an antibody to act as a receptor for the analyte of interest; binding occurs through ionic and van der Waals forces and is unrelated to properties of volatility, thermal stability, and chromogenicity. The high degree of selectivity in antibody binding allows quantification of trace chemicals. When surveying the wide range of analytical techniques available, the use of immunochemical techniques become inevitable for some chemicals, since immunoassays allow measurements not possible by other means. For example, thermal lability and low volatility prevent gas chromatographic (GC) analysis of some compounds, while lack of a distinctive chromophore may hamper liquid chromatographic (LC) analysis. For example, the thermal lability of pyrethroid insecticides can interfere with their analysis by GC, but they can be readily quantified by immunoassay. Plant, parasite, and fungus-derived toxins are usually too large for GC, but are well suited for immunoassay. Many new, biotechnology-derived insecticides pose particularly difficult analytical problems for conventional approaches because of their large mass, but antibodies to avermecatins and *Bacillus thuringiensis* toxins illustrate the applicability of immunoassays for insecticides in this upcoming class of compounds.

In the area of pesticide detection, many recently developed pesticides derive their species selectively by inhibiting specific enzymes in the target species. These substrates are often structural analogs of natural substrates, which means the chemist must determine trace levels of a pesticide in the presence of abundant amounts of the chemically-similar natural compound. With increasing public demands that pesticides not affect non-target species, the use of analogs of natural substrates will increase, and the selectivity of antibody binding offers an obvious solution to the problems of the residue analysis.

Unlike the sequential sample processing required by chromatographic methods, immunoassays allow for parallel sample processing and are inexpensive, rapid, and field-portable. In some cases immunoassays have been applied on site, resulting in additional savings in the costs and time involved in transporting samples back to a central laboratory. As screening assays, immunoassays can eliminate the need for complete work-up of negative samples, freeing the analytical laboratory to focus on the more interesting, positive samples. Ultimately, these cost savings make studies economically feasible that otherwise would be prohibitively expensive; for example, the mass screening of individual wells for drinking-water contamination, or the quantitative analysis of many epidemiologic studies. They also allow the introduction of monitoring programs in rural areas where skilled personnel and sophisticated laboratories are lacking. For many applications, the analytes must be extracted from the matrix, and some level of sample preparation and cleanup is required. However, sample cleanup is usually significantly less than is required for GC/MC analysis.

Immunoassays can be combined with other techniques to exploit the advantages of both methods. For example antibodies can be used to concentrate both the parent compound and its metabolitede from urine. Individual compounds then can be qualified by separating them by HPLC following immunoconcentration or as in the case of aflatoxin, immunopurification can then be followed by fluorescence detection, using intrinsic fluorescence of the analyte.

Applications of ImmunoAssays include monitoring of residues in foods, in the environment, and in humans for residues of both synthetic and naturally occurring toxins. The primary motives for thee development of these assays are their high sensitivity, high selectivity, portability, short analysis time, low cost, and potential for parallel processing samples. Parallel processing of samples means that immunoassays are highly applicable to mass screening studies either for monitoring regulatory compliance or for epidemiology studies. Particularly powerful analytical approaches use antibodies in conjuction with other methods, for example, the use of immunoaffinity columns to concentrate and purify the analyte before measurement by conventional means.

Examples of Particle-based Immunoassays

Microspheres or uniform particles of many sizes are used in a wide variety of modern diagnostic tests and assays. Particle-based diagnostic test qualitative/quantitative assays are usually based upon the specific interaction of antigen or analyte and antibody. Antigen or antibody can be adsorbed onto submicron sized polystyrene (PS) particles, often called "uniform latex particles". These sensitized particles then act to magnify or amplify the Antigen-Antibody reaction which takes place when a sample containing the sought molecule is mixed with the appropriately coated particles. In the classic example, a positive test results when uniformly dispersed milky appearing Ab-coated particles in a drop of water on a glass slide react with Ag in a drop of sample (whole blood, serum, urine, etc.) to cause particle agglutination (coagulation or clumping). An improvement in Latex Agglutination Tests (LATs) is the use of dyed particles which provide different contrast (dyed particles observed against a white background). They also permit some tests using samples of whole blood, if dark blue or black particles are used. As an example of the versatility of dyed particles, Wellcome Diagnostics (Dartford, Kent, England) has a Salmonella test which uses antibodies to three different antigen groups bound to three different colored particles (red, blue and green). By comparing the shade of the color of the combined agglutinated particles to a background color, one can decide which of seven combinations of Salmonella groups are present in the sample. Enzyme Immunofiltration Assays (EIFA) utilize microporous membranes as the receptor bearing solid phase and employ filtration as a means to hasten contact with the soluble sample ligand and the signal generating reagents. To prepare these tests, Ab (antibody) is adsorbed onto PS particles; the particles are caught on a filter and dried. In use: First, a sample is passed through a filter and any Ag (antigert) is caught by the Ab on the particles. Next, a second Ab-enzyme reacts with it to create an insoluble colored product which is proportional to the amount of Ag captured. The diffusion limitation of the reaction rate seen for conventional solid-phase immunoassays is minimized in EIFA. This is due to the flow of reactants through the receptor bearing membrane solid phase and the high ratio of microporous membrane surface area to liquid volume. Thus, EIFA permits rapid tests to be developed which reach completion in minutes. The antigen-antibody reactions in EIFA are visualized directly by immunostaining, in which the signal-generating conjugate yields colored spots at the reaction sites on the membrane. The color intensity of these spots can be quantitated by reflectance photometry.

Various EIFA methods have been described for the detection of antigens by means of direct binding of sample to the membrane or by employing two antibodies in a sandwich. Detection of antibodies by permutations of this method has also been described. In the sandwich assay described by Valkirs and Barton, rapid flow followed by a short incubation period was used to give a total assay time of 5 minutes. Quantitative assays based on EIFA have reproducibility and sensitivity comparable to that of other enzyme-linked immunosorbent assay (ELISA) techniques. The EIFA system can be incorporated in a unit which, besides, the antibody-bearing solid phase, includes an absorbing material for drawing liquid through the membrane and a waste reservoir. Because of their convenience, simplicity, and speed EIFA devices can be used in technically unsophisticated patient environments, i.e., as near patient tests. Various tests (like HCG, strep "A," and others) using this principle have been made by Hybritech (ICON). Abbott (TestPack), Novo Nordisk A/S (NovoClone Target), and many others. Murex SUDS use liquid reagents in their tests: mixing Ab-coated particles +Ag (from sample)+second Ab-enzyme conjugate; then pouring the mixture through their filter device to capture the particles which are rinsed with enzyme substrate to form color.

Improved Dyes and Latex

Small microspheres with bright, photostable fluorescent or colored dyes have opened up new opportunities for sensitive diagnostic tests. Fluorescent latex is inexpensive and widely applicable to qualitative and quantitative immunodiagnostics. The use of fluorescent latex particles should be applicable to most, if not all of the major latex-based diagnostic test systems presently in use, including latex agglutination tests (LAT), filter separation tests (in which agglutinated particles are trapped on a filter), particle capture ELISA methods and two-particle sandwich techniques. The increased signal available from fluorescence offers the option of quantitative, as well as qualitative results, with potential sensitivity increases of over 1000-fold, compared to colorimetric methods.

Several areas for latex particles in ultra-sensitive diagnostic tests are outlined as follows:

Latex Agglutination Tests (LAT)/Latex ImmunoAssay (LIA)

Agglutination/Capture Tests & Assays (Dyed Particles)

Particle Capture ELISA Tests & Assays

Dyed-Particle Sandwich Tests & Assays

SPRIA/SPEIA, DNA Probes (solid/liquid separation via centrifuge or magnet).

Membranes and filters have been used in a number of devices and in procedures for determining the presence of an analyte in a sample. These devices however, are dependent on a specific sample size, typically utilize bound reagents and are dependent upon rate of diffusion of liquid sample through an absorbent material to define the time limitations of the assay.

For example, U.S. Pat. No. 4,632,901 discloses an apparatus having a membrane or filter to which an antibody is bound and which is in liquid contact with an absorbent material. The sample size is limited by the absorbency of the material. U.S. Pat. No. 4,823,461 also discloses a membrane device having an absorbent material in fluid contact with the membrane. In this device, however, the absorbent material contacts only the periphery of the membrane thus causing liquid to diffuse transversely. The device is useful for only a limited number of sample types.

The invention is useful in detecting a broad range of analytes. U.S. Pat. No. 4,374,925 and 3,817,837 set out lists of analytes which are part of specific binding pairs. Analytes of particular interest include viruses, bacteria, fungi and other analytes of similar size. The examples of analytes that can be assayed with the present invention include Chlamydia, Salmonella, Bordetella, Candida and Aspergillus.

The development of a rapid on-site immunoassay system with a versatile and easy to use handheld meter provides an objective means of screening for levels of agricultural and environmental chemicals in either a remote site or laboratory setting and will enable better monitoring of the levels and movement of chemicals through the environment.

It is therefore desirable to provide an easy to handle apparatus which contains fluid samples holding analytes with a minimum chance for spillage and contamination between collection and laboratory. In addition, cells or sediment contained in the fluid have a valuable diagnostic use so that capturing the same for further testing is beneficial. In using the present invention testing can be performed quickly and accurately with minimum time. For some testing, particularly where antigens or analytes are being removed from the test fluid for a variety of tests, it is desirable to remove the antigens or analytes from the fluid so that various test procedures can be run. It is also desirable to do so with minimal exposure of laboratory personnel to the sample subject of testing. Previously this has been accomplished by a series of tests involving a number of different containers and expensive laboratory equipment. Mass testing using such a series of tests is expensive, time consuming, and often unsatisfactory.

SUMMARY OF THE INVENTION

There is provided in the practice of the invention, according to the presently preferred embodiment, an environmental analysis device allowing the detection of pesticide residues, mycotoxins, biomarkers of toxicity and industrial chemicals. This device is in the form of a tubular device having a removable cytology cup which contains a prefiltration/beads housing and cytology membrane for quantitative analysis and a transportable syringe in the housing with a coloration membrane for qualitative test analysis. A capture antibody is immobilized on the membrane surface of the syringe head which is in contact with the test fluid. After the body fluid sample is processed the prefilteration/beads housing becomes part of the cytology cup leaving the syringe head with membrane exposed. The cytology cup is then detached from the syringe body and the syringe body is inverted upside down to add the coloring reagents to the membrane.

If the screening test is positive (qualitative) for the specific analyte marker, the bead housing and the cytology cup will be sent to the reference laboratory for further analysis (quantitative). It is an object of the present invention to provide an inexpensive field palatable test. It is also an object of the invention to allow for parallel sample testing. It is additionally an object of the present invention to provide a testing device that can be used with minimal training and does not require skilled personnel.

In the accompanying drawings, there is shown an illustrative embodiment of the invention from which these and other of objectives, novel features and advantages will be readily apparent.

BRIEF DESCRIPTION OF THE DRAWINGS

FIG. 10 is an exploded cross sectional view of the bead housing removed from the cytology cup and fixative solution being added to the cytology membrane.

DETAILED DESCRIPTION OF THE INVENTION

Figure 1:
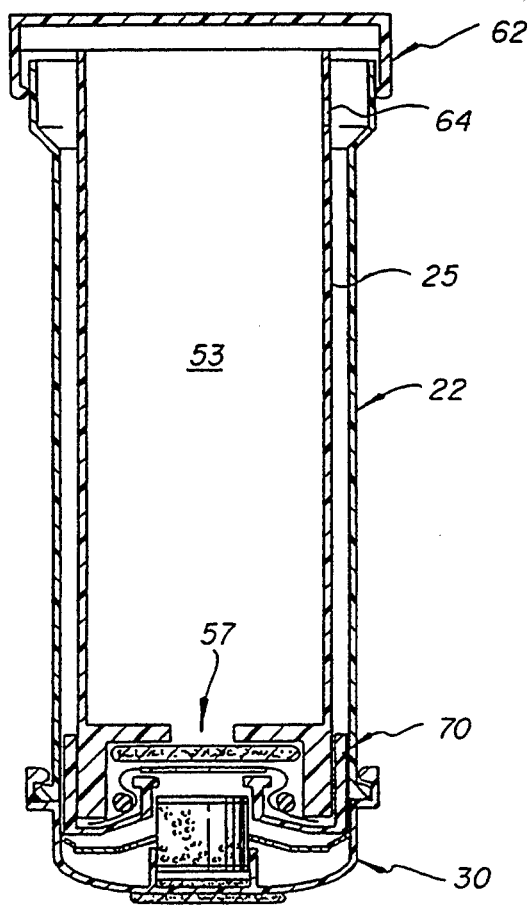
FIG. 1 is a cross sectional view of the assembled inventive membrane shuttle and cytology cup apparatus.

The preferred embodiment and best mode of the invention is seen in FIGS. 1 through 11. As used herein, "ligand-receptor pair" refers to a pair of compounds of which one, a "receptor" is capable of recognizing a particular binding site of the other ("ligand") or portion thereof, and is capable of binding to that compound for various ligands. Commonly, the receptor will be an antibody and the ligand will act as an antigen. Desirably, the analyte or an analyte derivative will be that ligand. Antibodies raised to hapten-protein complexes can be used to detect a variety of analytes that are structurally related to the hapten. Analytes in trace residue analysis include the parent compound, its metabolites and degradation products. As used herein, "analyte derivative" means a chemical derivative of an analyte that retains the capacity to bind to the other member of a ligand-receptor pair as does the analyte. Lists of analytes which are part of specific binding pairs are set forth in U.S. Pat. No. 4,374,925 and U.S. Pat. No. 3,817,837 which patents are incorporated by reference and made part of this specification. The use of the term "labeled member of a ligand-receptor pair" means a conjugate of a ligand-receptor pair member with a signal producing material (I.E. colored particles) or a chemical label such as an enzyme, a fluorescent compound or other detectable chemical species, the conjugate retaining the capacity to bind to the other member of the ligand-receptor pair, and the other detectable label continuing to have a capacity of being detected by a detector system (which may be a separate chemical reaction system) to provide a perceptible signal. "Detector," "label detector". Several convenient, known chromogens are available which produce visible color when added to their specific enzymes and substrates.

While the invention can be used for the testing of any fluid, it is primarily designed for use in collecting samples for use in testing for the presence of various kinds of toxic analytes, such as benzene, cadmium, carbon tetrachloride, chloroform, chromium cyanide, dichloromethane, lead, mercury, methyl ethyl ketone, methyl isobutyl ketone, tetrachloroethylene, toluene, trichloroethane, trichloroethylene and xylene.

In addition to the aforementioned toxic analyte, the invention can be used to determine the presence of fungal toxins or mycotoxins in foods and animal feeding stuffs. Mycotoxin contamination of animal feeds occur as a result of invasion of crop by field fungi or the growth of fungi in crops stored under less than ideal conditions. The toxicity of mycotoxins in general and the carcinogenic potential of aflatoxins in particular are well documented. Significant aflatoxin-contamination can occur in crops such as corn and cereals, which are major constituents of animal feeds. The potential, therefore, exists that aflatoxin in feed can be left as residue in meat, milk or eggs.

One of the key analyses performed in microbiological testing laboratories is the detection of Salmonella. All known Salmonella species are pathogenic to man and/or animals and cause the well-known Salmonellosis infection.

Surveillance of salmonellae by the 6-step conventional culture method (6) is both costly and time-consuming—a negative test requiring a minimum of 96 hours and a positive test at least an additional 24 hours.

Another use of the present invention is to test for Sulphamethazine residues and the presence of herbicides. Sulphonamides are used in veterinary practice as antibacterial agents. The use of suphamethazine in swine has made it the single most prevalent residue of all drugs used. Sulphamethazine (SMZ) at levels of 0.011% may be added to starter and pre-starter feeds to be used in the control of atrophic rhinitis, maintenance of growth rate, and feed efficiency.

Fusilade is the trade name for the active ingredient fluazifop-butyl which is a potent selective herbicide used to control grass weeds in many crops such as sugarbeets, soybeans, rapeseed etc.

Another use of the present invention is to test for specific DNA and RNA. There are a large number of different protocols for the isolation of nucleic acids. Most of the methods are geared toward the isolation of highly purified samples, and DNA or RNA obtained by many of these procedures is suitable for use in PCR amplifications. Several good protocols have been described in detail (Davis et al. 1986; Ausubel et al. 1987; Berger and Kimmel 1987). Rapid methods that do not involve extensive purification of the nucleic acids yet yield preparations that can be used for amplification of DNA and/or RNA sequences are also described by Ernest S. Kawasaki in PCR Protocols: A Guide to Methods and Applications, 1990. Kawasaki's simplified method involve the use of nonionic detergents and Proteinase K to solubilize DNA from cells in PCR buffer or TE Laureth 12 and Tween 20 at 0.5%. These DNA extraction methods are compatible with Taq polymerase reverse transcriptase and work well in the presence of up to 1% NP-40. Proteinase K is a very good protease for digesting nuclei or whole cells to release DNA or RNA into a form readily accessible to the polymerases. It has the advantage of being relatively heat stable in the mid-temperature range 50 to 60 degrees Celcius, yet can be thermally inactivated easily at 95 degrees Celcius.

The following protocols were adapted from Ernest S. Kawasaki (PCR Protocols: A Guide to Methods and Applications, 1990) for use with the invention.

Reagents for DNA and RNA Isolation

Proteinase K: Dissolved at 20 mg/ml in 10 mM Tris-Cl (pH 7.5). Obtained from Boehringer-Mannheim or Bethesda Research Labs.

FungiBact: Obtained from Irvine-Scientific.

Tris-EDTA BUFFER (TE):10 mM Tris-Cl, 1 mM EDTA (ph 7.5 or 8.0)

PBS: Phosophate buffered saline.

PCR buffer without gelatin or bovine serum albumin: 50 mM KCl, 10-20 mM Tris-Cl, 2.5 mM MgCl2 (pH 8.3).

Detergents: Laureth 12 (Mazer Chemicals, Gurnee, Ill.), NP-40, and Tween 20, highest purity.

K buffer: PCR buffer without gelatin or bovine serum albumin, containing 1% Laureth 12 or 0.5% Tween 20, and 100 ug/ml of fresh Proteinase K.

Figure 2:
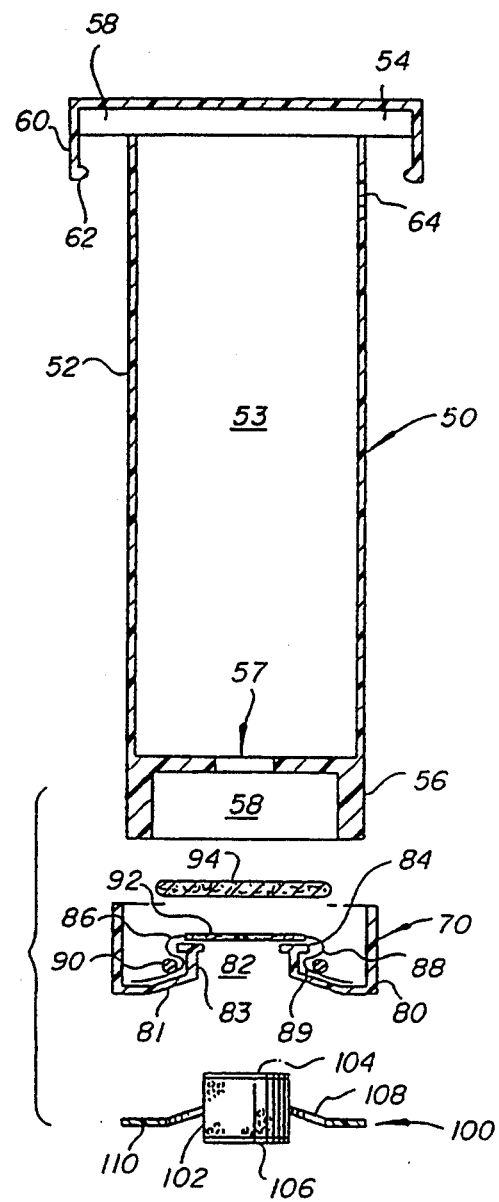
FIG. 2 is an exploded cross sectional view of the piston assembly and test assembly which fits into the cytology cup of FIG. 1.
Figure 3:
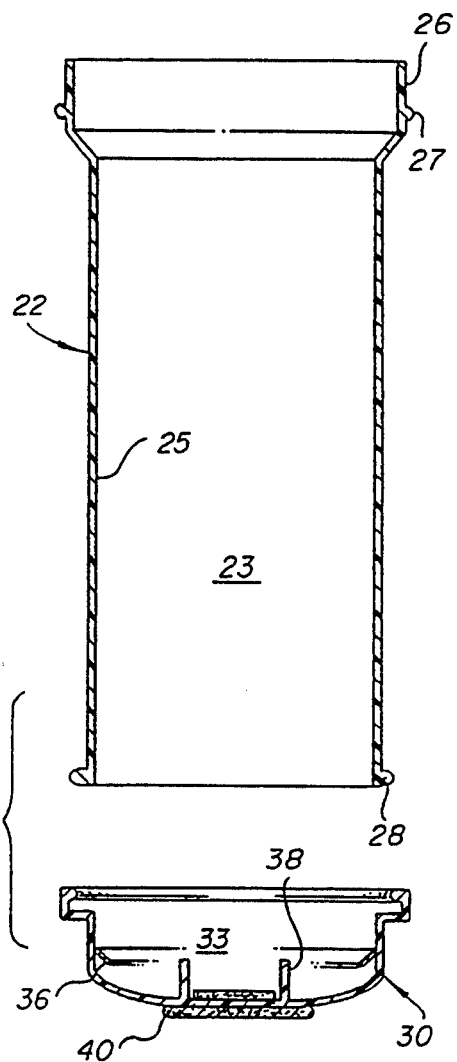
FIG. 3 is a cross sectional view of exploded parts of the tubular collection assembly and cytology cup.
Figure 4:
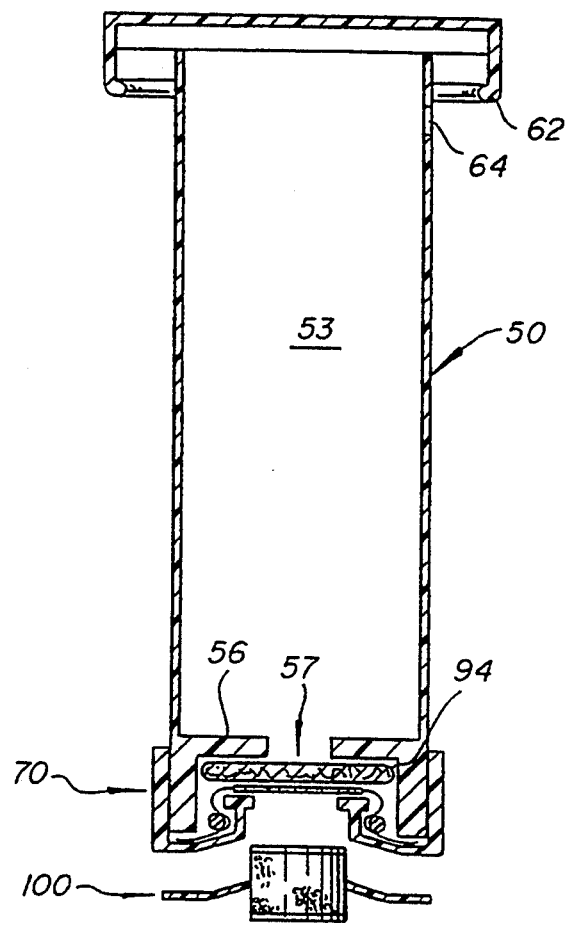
FIG. 4 is an exploded cross sectional piston assembly and prefilteration bead housing unit.

As shown in FIGS. 1-3, a sample testing apparatus 20 is constructed of polystyrene and comprises a tubular collection unit or syringe barrel 22, a cytology cup and a piston 50 with associated piston head test assembly 70.

The tubular collection unit or syringe barrel 22 is constructed with a tubular open ended cylindrical body 24 defining a chamber 23 with an open flared end portion 26 and circular locking rib 27 formed on one end and on the other end a circular locking rib 28. The flared end portion 26 has a wide mouth to more easily receive the test fluid which is loaded into the chamber. It should be noted that a prelabelled antibody is added to the fluid sample along with the buffer reagents.

A cytology cup 30 is removably secured to the body 24 by virtue of a snap on fit of the cups locking mechanism over the rib 28. The cytology cup 30 comprises a cylindrical cup shaped body 32 with a locking lip mechanism comprising a stepped portion 33 and a flexible lip member 34 ending in rib 35. The lip rib 35 has an inner lesser diameter than the outer diameter of rib 28, allowing rib 28 to be snap fit into the locking lip mechanism. A downwardly extending circular flange member 36 extends inwardly toward the chamber of the cup to hold a bead housing assembly 100 in place in the cytology cup 30. The cytology cup is also provided with a cytology membrane housing comprised of a cylindrical barrel body 38 and an end member 39. The cytology membrane housing is removably mounted or secured in an aperture formed in the bottom surface of the body 32 with the barrel 38 extending upward into the chamber and the end member seated adjacent the bottom surface of the cytology cup 30. The barrel 38 holds a cytology membrane 40 which is seated on end member 39 at the bottom of the cup where cells, organisms and sediments can be captured at the end of the assay. The preferred membrane 40 which is used is manufactured by Nuclepore and can be cut in discs ranging from 13 mm to 293 mm in diameter with a pore size larger than 1.0 um and exhibits a tensile strength of over 3000 psi. The preferred material composition is polycarbonate although polyester can be used. The membrane is flexible and will not crack and is resistent to splitting or breakage. These membrane filters have a pore size, pore density and pore structure which are geometrically defined and photomicrographs of the same reveal individual pore openings on the surface with diameters closely equal to the rated pore size of the membrane. The advantages of a defined surface pore size are the complete surface capture of all particulate larger than the rated pore size, excellent particulate visibility and internal reference scale for particulate sizing.

The smooth flat surface of the membrane offers an ideal substrate for particulate analysis using either optical or electron microscopy. The pore size of the filter used in the invention will vary according to the analyte being assayed for and the type of sample. The pores should be sized according to the particular analyte for which the assay is being performed which is in present invention is preferably directed to toxic analytes such as benzene, cadmium, carbon tetrachloride, chloroform, chromium, cyanide, dichloromethane, lead mercury, methyl ethyl ketone, methyl isobutyl ketone, nickle, tetrachloroethylene, toluene, trichloroethane and xylene. When the subject analyte is bound to the labeled ligand receptor pair member the resulting complex is prevented from passing through the filter. Although the pore size of the filter may be larger than the average diameter of the organism being assayed in order to obtain adequate sensitivity of the assay, the pore size is desirable to be no more than 2.5 times as large as the analyte being assayed. Filters with pore sizes ranging from 0.1 um in diameter to 100 um in diameter have been used with this invention. Preferably, filters having pores sized no larger than about 15 um are used. Those membranes with pore size larger than 1.0 um are sufficiently transparent to permit transmitted light allowing viewing of objects on the membrane surface without cleaning the membrane. The membrane can be coated with a hydrophilic surface that yields nearly instantanous flash-wetting with aqueous solutions. Such membranes when coated are coated with polyvinylphrrolidone (PVP) to render them hydrophilic. However the membrane can be PVP free if so desired.

Thus the cytology cup diagnostic membrane 40 has a smooth flat surface which is ideal for the collection of materials from all types of fluids. Polycarbonate membranes are semi-transparent permitting direct microscopy or may easily be dissolved to remove all pore image artifacts. Thus the advantages which occur in the use of a polycarbonate membrane are minimum clogging by red blood cells and protein, well preserved cellular morphology with high recovery rate, rapid filtration with low pressure, and excellent surface capture due to the pore structure and porosity. The smooth flat surface permits high cell visibility, improved morphologic resolution and surface capture. The membrane thickness allows easy mounting and immediate microscopic examination. The membrane's low absorption and adsoption provides improved contrast, greater cell isolation and easy mounting while its non-staining characteristics allow improved contrast and simpler microscopic analysis. Furthermore the chemical resistance of the membrane is unaffected by conventioned cytologic fixatives and stains. The barrel also serves as a holder for the bead housing assembly.

A piston 50 as shown in FIG. 2 is designed to fit within the cylindrical body of the syringe barrel 24 and slideably move along the interior wall surface 25 holding a test assembly 70 for deposit within the cytology cup. The piston 50 is constructed of a transparent plastic and comprises a hollow cylindrical piston body 52 provided with a thumb cover assembly 54 and and a cross sectional U-shaped bottom end member 56 of thicker construction than the piston body 52. The thumb cover assembly 54 includes a thumb support member 58 with a downwardly projecting flexible skirt or flange 60 ending in locking rib 62. The locking rib 62 is adapted to lock onto syringe rib 27 as the rib 27 engages rib 62 to cam the flange 60 so that it springs outward allowing rib 62 to ride over rib 27 and then snap back into place thereby securing the piston 50 on the syringe barrel 22. An air release aperture 64 is formed in the piston body so that there is communication between the interior chamber 53 of the piston body and the outside atmosphere. The bottom endwall 56 is provided with a throughgoing aperture 57 which allows communication with the chamber 53.

Figure 5:
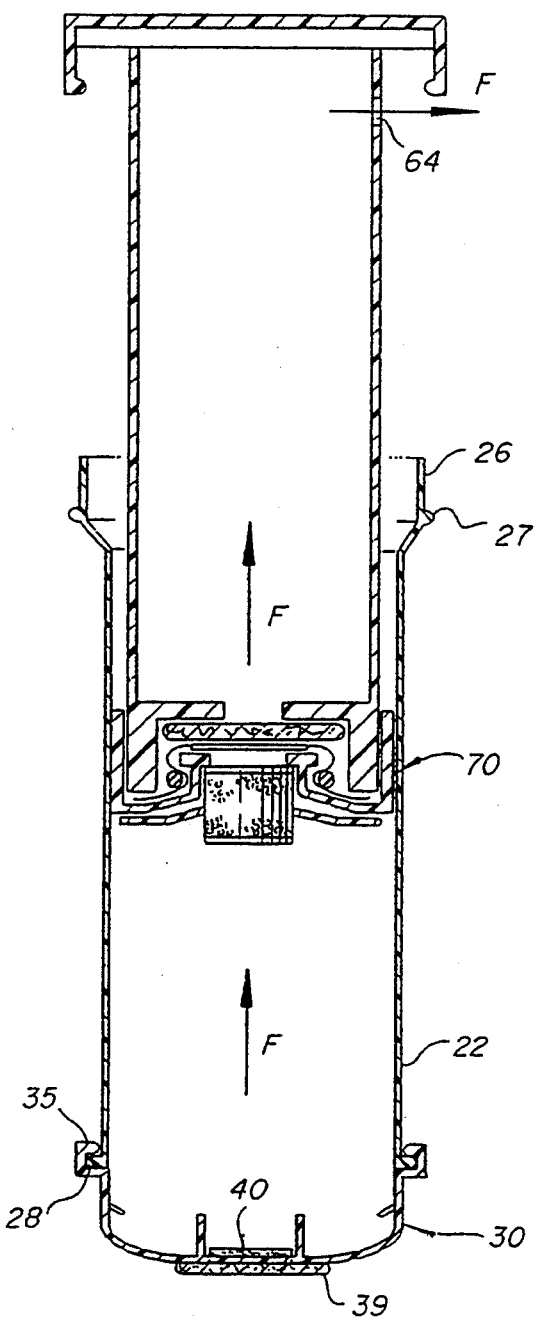
FIG. 5 is a cross sectional view of the assembled membrane shuttle and cytology cup apparatus with direction of movement of the fluid being shown by arrows F.

The test assembly 70 as shown in exploded parts in FIG. 2 is constructed with a cylindrical base cap shaped member 80 having an interior diameter equal to or slightly less than the exterior diameter of endwall 56 so that it can be friction fit on same and a funnel shaped endwall 81 which funnels into a cylindrical section 83 which serves as a chamber for housing body 102 and a support for seat 84. The endwall by virtue of section 83 is provided with a pass through port or opening 82. The port 82 is substantially covered by a circular ring shaped membrane disk seat 84 which sits over the port. The seat 84 is provided with a flat upper surface to hold membrane 92 and a flat lower surface forming a stop for the body 102 of the bead housing assembly. A membrane clip assembly 86 with a curved spring skirt 88 is mounted over the disc seat 84 and curls back under the disc seat 84 toward cylindrical section 83 forming a circular channel 89 and then extends outward along the inner surface 81 of the base member body 80 to provide a tight fit for attachment of the membrane clip assembly to the rim of the disc seat 84. An elastomeric "O" ring 90 abuts the surface of the skirt 88 in channel 89 to hold the membrane clip assembly tightly on the disc seat and the membrane 92 positioned over port 82. The plastic membrane member 92 is provided with immobilized ligands preferably in the form of antibodies and is seated on disc seat 84 over port 82. A porous support disc member 94 provides support for membrane 92 against the fluid flow coming through port 82 and sits in the endwall cavity 58 over port 57 so that the fluid pressure will not rupture the membrane 92. Thus the disc support member 94 sits in the cavity 58 of bottom end member 56 as is shown in FIG. 5. Opposite the membrane member 92 on the opposite side of the disc seat 84, a prefilteration bead housing assembly 100 is seated in cavity 82 formed by cylindrical section 83 against the back of disc seat 84 which as noted operates as a stop. All of the parts of the membrane clip assembly are preferably integrally molded in one piece.

The bead housing assembly 100 is constructed with a barrel shaped cylindrical body 102 open at both ends and threaded to allow the mounting of circular top cover 104 and bottom cover 106 which are threadably mounted on the inside of the cylindrical body. These endwalls are provided with throughgoing perforations or apertures or are formed with porous septums to allow easy flowthrough of fluids. A saucer shaped housing support member 108 with a flat rim 110 is contoured to fit around the outer surface of cylindrical body 102 and keeps the bead housing from contacting cytology membrane 40 while locking the bead housing in the chamber of the cytology cup under rib 36. While the bead housing is preferably used for prefilteration of the body fluids used for screening and cytology it alternately can be filled with resin material to collect antigen for quantitative studies. In this regard, bead housing body 102 may be filled with resin/sample consisting of beads of all forms and sizes which can be specifically manufactured for ion exchange (e.g., fast flow Q-sepharose anion exchange, and Fast Flow S-sepharose cation exchange from Pharmacia), high affinity chromatography or hydrophobicity (e.g., phenylsepharose beads). Preferably, the module holds high affinity resin with specific antibodies immobilized onto the solid phase resin (e.g., protein A, etc. ) so that anitgens in the sample can bind to their specific antibodies while passing through the resin module and become immobilized as well.

Figure 6:
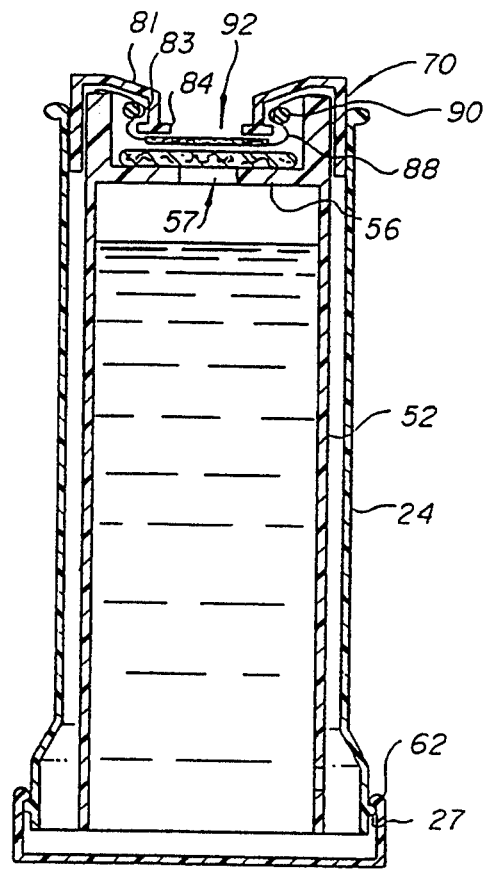
FIG. 6 is an inverted cross sectional view of the collection tube and piston assembly, collection tube and membrane testing module positioned for the membrane screening test.
Figure 7:
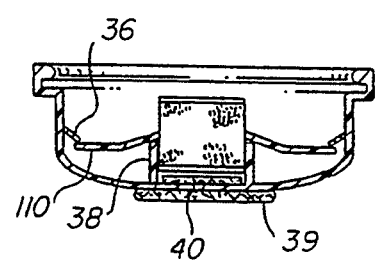
FIG. 7 is a cross sectional view of the separated cytology cup assembly.
Figure 8:
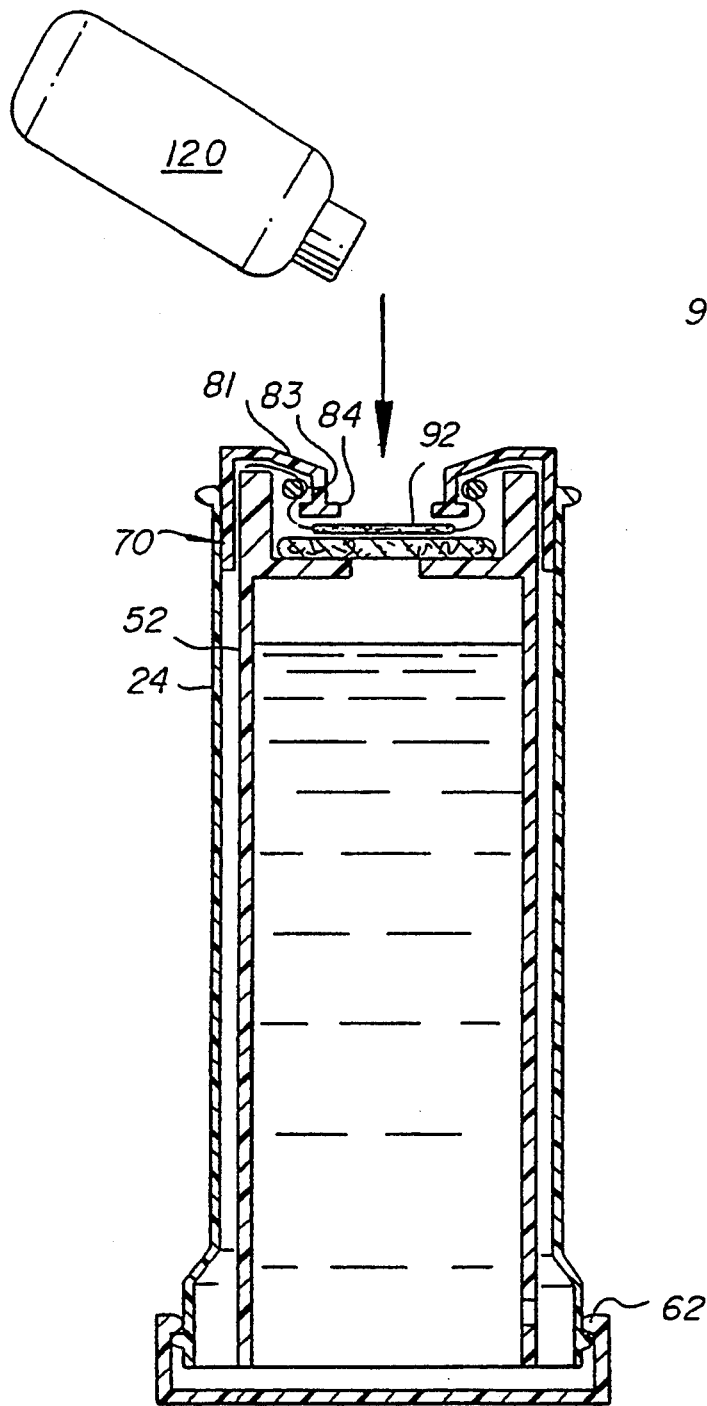
FIG. 8 is a cross sectional view of the apparatus shown in FIG. 6 showing color developing solution being added to the testing membrane.

It should be noted that the air contained in chamber 53 is pushed out by the fluid entering through port 57 into chamber 53, through air release aperture 64 into a chamber formed by the concentric outer surface of the piston body 52 and the inner surface 25 of syringe barrel 22. The test assembly 70 is pushed down by the piston body until it enters into the body cavity 33 of the cytology cup 30 past the spring rib 36. At this time the lower surface of the rim 110 of bead housing support 108 engages and deflects the spring rib 36 thus seating the bead housing 100 in a predetermined position held in the cytology cup. The body fluid entering the body chamber 53 through port 57 will be trapped inside it even after removal of the cytology cup 30 as shown in FIG. 6.

The membrane surface 92 is provided with immobilized antibodies which having had flow contact with the test fluid captures the specific component of the fluid which is to be tested in this example, analytes of specific toxins. The cytology cup 30 is then pulled off of the syringe barrel 22 with the bead housing 100 contained therein. The piston 50 remains with the syringe barrel 22 and test assembly 70, so when the same is inverted membrane 92 can be tested with a color developing solution as seen in FIGS. 10(a)-(c).

The fluid which will be placed in compartments 23 and 33 (see FIGS. 7-8) contains lyophilized primary labelled antibodies having a binding site contoured to the epitope structure and chemistry of an antigen or analyte which has been previously determined as being a marker for a specific type of toxin. The antibodies are labelled with HRP (horseradish peroxidase), an enzyme that detoxifies hydrogen peroxide, $H_2O_2$, by converting it to water. HRP initiates this transformation when it gives hydrogen peroxide a pair of electrons. The enzyme subsequently collects these electrons from suitable donors. Thus the total color generated by peroxidase depends upon the relative rates of color generation and product inactivation of the enzyme. Membrane 92 contains antibodies immobilized (covalently bound) thereto in area 93 for reception of the complexed antibodies and is provided with a second area 95 which acts as a control. The antigen or analyte has epitopes which have a high affinity for the binding sites of the primary labelled antibody and immobilized antibody. The principle of affinity chromatography requires that a successful separation of a biospecific ligand is available and that it can be chemically immobilized to a chromatographic bed material, the matrix. Numbers of methods well known in the art have been used to couple or immobilize the antibodies to a variety of matrixes. Examples of immobilization techniques that exhibit variable linkage are those formed by the reaction of the reactive groups on the support with amino, thiol, hydroxyl, and carboxyl groups on the protein ligand. The selection of the ligand is influenced by two factors. First, the ligand should exhibit specific and reversible binding affinity for the substance to be purified and secondly it should have chemically modifiable groups which allow it to be attached to the matrix without destroying its binding activity (Examples of such are Protein G Sepharose manufactured by Pharmacia, Hydrazide AvidGel Ax manufactured by BioProbe International, and Actigel-ALD manufactured by Sterogene Bioseparation Inc.).

An advantage to the use of Actigel-ALD is that it does not cross link proteins therefore allowing proteins to retain high bioactivity after their immobilization. Actigel-ALO SUPER FLOW, also available from Sterogene Bioseparation Inc., permits a linear flow rate of up to 3000 cm/h which would fit nicely with the flow rates in the apparatus.

After the fluid mixed with prelabelled antigen has passed over the membrane 92 and deposited complexed ligands on the immobilized antibodies, the membrane 92 is preferably soaked with ABTS solution 120 to determine the presence of the disease marker. A hydrogen peroxide ($H_2O_2$) solution may be alternately placed on the membrane when OPD or TMB or other dual substrate systems are used.

The color solution 120 used on the membrane 92 is preferably a substrate manufactured by Kirkegaard & Perry Labs under one of several acronyms namely: ABTS (2,2'-azino-di-[3-ethylbenzthiazoline sulfonate (6)]; OPD (orthophenylene diamine); or TMB (tetramethylkbenzidine). In choosing the substrate, the sensitivity of the immunoassay is determined by the discrimination of the antibody reagents. When this occurs, the use of a more sensitive substrate serves only to proportionately increase the signal and the background. The result is more color but the same signal-to-noise ratio. Should the more sensitive substrate push the absorbance over the cut-off of the reader, the faster substrate may in fact reduce the signal-to-noise ratio.

Figure 9A:
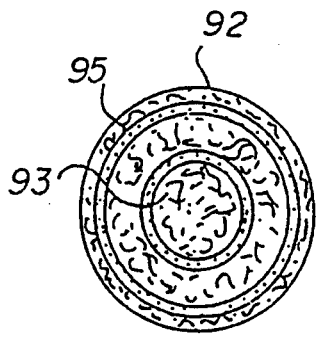
FIGS. 9(a); 9(b) and 9(c) are top plan views of the testing membrane shown in FIG. 8 showing positive, negative and bad reagent test results.
Figure 9B:
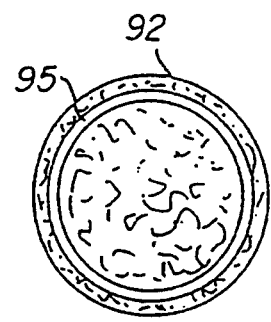
Figure 9C:
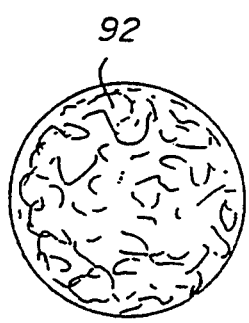

The preferred color solution 120 as shown in FIG. 9 of the present invention is ABTS. The preferred ABTS substrate is a one-component substrate. The HRP label on the primary antibody is turned by the ABTS to a blue-green color and there is no change in color or absorbance when the reaction is stopped with SDS (sodium dodecyl sulfate). If the assay optimization indicates that the sensitivity of the immunoassay is limited by the color generated by the HRP substrate, then the more sensitive TMB substrate would give more color development without a corresponding increase in the background. Another advantage of the TMB substrate is that it often lowers the amount of antibody and antigen reagents required for the immunoassay. TMB substrate is a two component liquid substrate and requires hydrogen peroxide. HRP converts TMB to a blue product. When the reaction is stopped by acidification, the TMB product becomes yellow. ODP is generally provided as a tablet that is dissolved in buffer at the time of use. HRP converts OPD to a yellow product which continues to oxidize into a brown precipitate. Upon acidification the OPD product becomes orange.

The membrane material 92 with matrix and immobilized ligand (in this case immobilized antibody) having had flow contact with the fluid, captures through antigen-antibody reaction or immune reaction the specific ligand component carried by the fluid, namely, the complexed primary labelled antibody and antigen-/analyte which was formerly contained by the body fluid in chambers 23 and 33. This antibody as previously noted was provided prelabelled with coloring enzyme HRP. When the specific antigen/analyte is present in the testing sample which is added to the container, the antigen/analyte reacts with the antibody to form antigen-antibody complexes. This labelling enzyme of the antibody reacts with the ABTS poured on the membrane surface 92 turning the surface of the membrane 93 into a blue green color. If there is an absence of the antigen/analyte in the specimen sample, the antibody will remain unoccupied and will not bind to the immobilized antibodies. On the other hand, if the antigen-/analyte is present, anitgen-antibody complexes will be formed and held on the membrane surface for reaction with the ABTS solution. The degree of color developed should correlate with the amount of prelabelled antibody/antigen/analyte complexes which in turn correlates with the amount of antigen/analyte present in the sample. The positive control area 93 reflects the current state of the coloring reagents as well as the prelabelled antibody at the time the test is performed.

In the foregoing description, the invention has been described with reference to a particular preferred embodiment, although it is to be understood that specific details shown are merely illustrative, and the invention may be carried out in other ways without departing from the true spirit and scope of the following claims:

What is claimed is:

1. An apparatus for collecting environmental, biological and physiological samples for quantitative and qualitative testing of at least one analyte in a sample, comprising a tubular container having open ends; a particulate collection cup removably secured to one end of said container, said particulate collection cup including a cytology membrane, a piston assembly slidably mounted in said tubular container, said piston assembly comprising a hollow piston body with an internal surface defining a chamber, an opening formed in an end face of said piston body, a membrane based immunoassay test assembly with immobilized a member of a ligand-receptor specific binding pair secured across said opening of said piston body and a removable bead housing assembly in mating engagement with said membrane based immunoassay test assembly, said bead housing having an aperture allowing fluid flow therethrough to contact the membrane based immunoassay test assembly.

2. An apparatus for collecting environmental, biological and physiological samples for quantitative and qualitative testing of at least one analyte in a sample according to claim 1 wherein said cytology membrane is a sponge.

3. An apparatus as claimed in claim 1 wherein the member of an immobilized ligand-receptor specific binding pair test for a binding site on an antigen complex.

4. An apparatus as claimed in claim 1 wherein said immobilized ligand-receptor specific binding pair test for a binding site on Chlamydia.

5. An apparatus as claimed in claim 1 wherein said immobilized ligand-receptor specific binding pair test for a binding site on Salmonella.

6. An apparatus as claimed in claim 1 wherein said immobilized ligand-receptor specific binding pair test for a binding site on Bordetella.

7. An apparatus as claimed in claim 1 wherein said immobilized ligand-receptor specific binding pair test for a binding site on Candida.

8. An apparatus as claimed in claim 1 wherein said immobilized ligand-receptor specific binding pair test for a binding site on Aspergillus.

9. An apparatus as claimed in claim 1 wherein said immobilized ligand-receptor specific binding pair test for a binding site on DNA.

10. An apparatus as claimed in claim 1 wherein said immobilized ligand-receptor specific binding pair test for a binding site on RNA.

11. An apparatus according to claim 1, further including a lockable cap member provided on one end of said piston body.

12. An apparatus according to claim 1 wherein said particulate collection cup includes a stop rib.

13. An apparatus for collecting environmental, biological and physiological samples for qualitative testing of at least one analyte in a sample, comprising a container having open ends; a cap removably secured to a lower end of said container, said cap including a cytology membrane; a piston assembly slidably mounted in said container, said piston assembly comprising a hollow piston body with an internal surface defining a chamber, fluid flow means formed in an end face of said piston body for flow of fluid into and out of said piston body, a cap member covering an upper end of said piston body, said cap member being provided with locking means allowing it to be locked onto said container, a membrane based immunoassay test assembly having immobilized a member of a ligand-receptor specific binding pair removably secured to said piston body and a removable bead housing assembly in mating engagement with said membrane based immunoassay test assembly, said cylindrical bead housing assembly having an aperture allowing fluid flow therethrough to contact the membrane based immunoassay test assembly.

14. An apparatus for testing for toxic analytes in environmental, biological and physiological samples comprising a fluid container having a first open and a second open end, a specimen test assembly moveably mounted in said first open end of said fluid container, said specimen test assembly comprising piston means with a membrane provided with immobilized ligand means capable of recognizing a binding site of another ligand a bead housing assembly removably mounted on said specimen test assembly and cytology means mounted on said fluid container, said cytology means including a porous cytology membrane, said porous cytology membrane having pores smaller than a particulate marker to be isolated, said membrane provided with an immobilized ligand which specifically binds to and captures a predetermined amount of analyte for qualitative analysis.

15. An apparatus for testing for toxic analytes in environmental, biological and physiological samples as claimed in claim 14 wherein said immobilized ligand specifically binds to a binding site on a DNA polynucleotide.

16. An apparatus for testing for toxic analytes in environmental, biological and physiological samples as claimed in claim 14 wherein said immobilized ligand specifically binds to a binding site on a RNA polynucleotide.

17. An apparatus for testing for toxic analytes in environmental, biological and physiological samples as claimed in claim 14 wherein said immobilized ligand specifically binds to a binding site on a conjugate of a ligand-receptor pair member and a signal producing material.

18. An apparatus for testing for toxic analytes in environmental, biological and physiological samples as claimed in claim 14 wherein said immobilized ligand specifically bind to a binding site on a heavy metal.

19. An apparatus for testing for toxic analytes in environmental, biological and physiological samples as claimed in claim 14 wherein said immobilized ligand specifically binds to a binding site on a conjugate of a ligand-receptor pair member and a dyed particle.

20. An apparatus for testing for toxic analytes in an environmental sample comprising a fluid container with removable particulate cup means, a specimen test assembly comprising piston means, a membrane assembly mounted in said piston means, said membrane assembly including a membrane provided with immobilized antibodies which specifically bind to and capture a predetermined amount of antigen and a housing means removably mounted to said membrane assembly in a first position and locatably associated with said removable particulate cup means in a second position, said housing means comprising a housing containing fluid filter and particulate capture means.

21. An apparatus for testing for toxic analytes as claimed in claim 20 wherein said immobilized antibodies are selected to capture toxic analytes selected from the group consisting of benzene, cadmium, carbon tetrachloride, chloroform, chromium cyanide, dichloromethane, lead, mercury, methyl ethyl ketone, methyl isobutyl ketone, tetrachloroethylene, toluene, trichloroethane, trichloroethylene and xylene.

22. An apparatus for testing for toxic analytes as claimed in claim 20 wherein said immobilized antibodies are selected to capture a mycotoxin.

23. An apparatus for testing for toxic analytes as claimed in claim 20 wherein said immobilized antibodies are selected to capture a fungal toxin.

24. An apparatus for testing for toxic analytes as claimed in claim 20 wherein said immobilized antibodies are selected to capture a sulphamethazine residue.

25. An apparatus for testing for toxic analytes as claimed in claim 20 wherein said immobilized antibodies are selected to capture a herbicide.

26. An apparatus for testing for toxic analytes of interest as claimed in claim 20 wherein said membrane has a pore size of 15 um or less.

27. A device for separation and removal of particulate matter and for qualitative and/or quantitative determination of the presence of at least one analyte in a liquid biological sample comprising:

a hollow cylinder;

a particulate collection receptacle removably secured at and in fluid communication with one open end of said cylinder;

a particulate-retaining porous membrane in said particulate collection receptacle;

a hollow piston slidably movable within said hollow cylinder and having an opening in the end of said piston closest to said particulate collection receptacle, said end of said piston and walls of said hollow cylinder defining a first chamber, said end of said piston and walls of said piston defining a second chamber and said opening providing fluid communication between said first and second chambers; and a microporous test membrane across said opening having immobilized thereon at least one receptor which specifically binds with at least one analyte.

28. A device according to claim 27 wherein said microporous test membrane is located downstream of said particulate-retaining porous membrane.

29. A device according to claim 27 wherein said microporous test membrane is mounted within a recess in said end of said piston.

30. A device according to claim 27, further including a cap secured to the end of said hollow piston opposite said opening providing fluid sealing of an open end of said hollow cylinder opposite said open end to which said particulate collection receptacle is removable secured and in which said piston is inserted.

* * * * *